United States Patent [19]

Pagani

[11] 4,320,103
[45] Mar. 16, 1982

[54] FLEXIBLE INTEGRATED METHOD FOR THE PRODUCTION OF AMMONIA AND UREA

[75] Inventor: Giorgio Pagani, Milan, Italy

[73] Assignee: Snamprogetti S.p.A., Milan, Italy

[21] Appl. No.: 184,175

[22] Filed: Sep. 4, 1980

Related U.S. Application Data

[63] Continuation of Ser. No. 54,484, Jul. 3, 1979, abandoned, which is a continuation-in-part of Ser. No. 867,974, Jan. 9, 1978, abandoned, which is a continuation of Ser. No. 670,729, Mar. 26, 1976, abandoned.

[30] Foreign Application Priority Data

Mar. 28, 1975 [IT]  Italy .............................. 21778 A/75

[51] Int. Cl.³ ..................... C01C 1/04; C07C 126/00
[52] U.S. Cl. ..................................... 423/359; 564/66; 564/69
[58] Field of Search .................. 423/359; 564/63–73

[56] References Cited

U.S. PATENT DOCUMENTS

| | | | |
|---|---|---|---|
| 3,303,215 | 2/1967 | Otsuka et al. | 564/69 |
| 3,310,376 | 3/1967 | Cook et al. | 564/69 |
| 3,349,126 | 10/1967 | Hsu et al. | 564/66 |
| 3,640,052 | 2/1972 | Konoki et al. | 564/73 X |
| 3,684,442 | 8/1972 | Knoki et al. | 564/73 X |
| 4,012,443 | 3/1977 | Bonetti | 564/66 |
| 4,013,718 | 3/1977 | Guadalupi et al. | 564/69 |

Primary Examiner—Edward J. Meros
Attorney, Agent, or Firm—Morgan, Finnegan, Pine, Foley & Lee

[57] ABSTRACT

In an integrated flexible installation for producing ammonia and urea, the improved method which consists in that a portion of the gaseous stream comprising carbon dioxide, hydrogen and nitrogen is fed to a complementary decarbonation area and then admixed with a portion of a similar, but non-decarbonated stream of gas prior to entering the carbon-dioxide-absorption unit. Liquid ammonia is recovered from a portion of the ammoniated aqueous solution used for abating the ammonia and sent to a distillation column to recover liquid ammonia therefrom.

2 Claims, 1 Drawing Figure

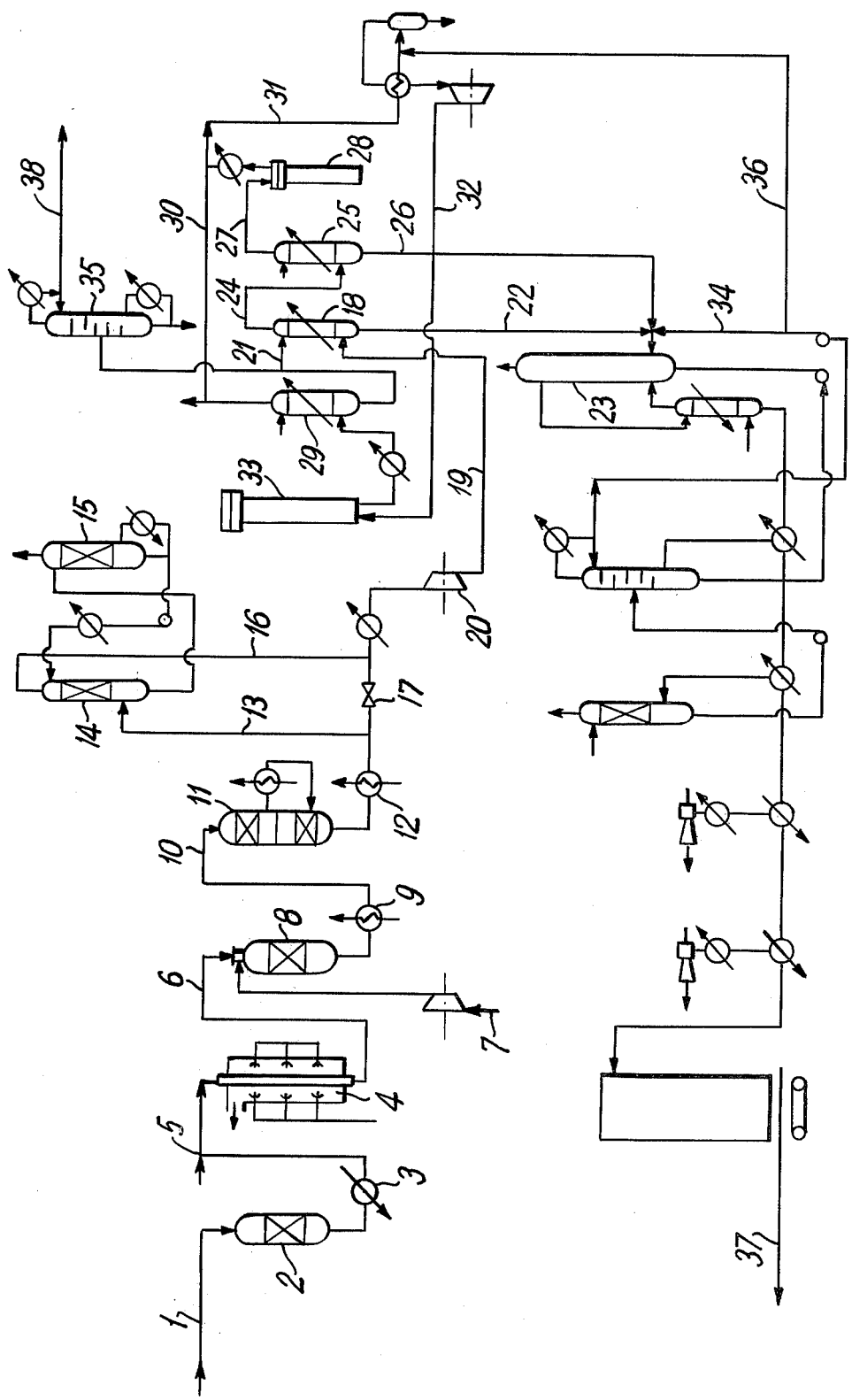

FLEXIBLE INTEGRATED METHOD FOR THE PRODUCTION OF AMMONIA AND UREA

CROSS REFERENCE TO RELATED APPLICATIONS

This is a rule 60 continuation application of Ser. No. 054,484 filed on July 3, 1979, now abandoned, which is a continuation-in-part application of Ser. No. 867,974 filed Jan. 9, 1978, now abandoned, which in turn is a continuation application of Ser. No. 670,729 filed Mar. 26, 1976, now abandoned, and which claims the priority of Italian application Ser. No. 21778 A/75 filed on Mar. 28, 1975.

This invention relates to a flexible integrated process for the production of ammonia and urea.

Integrated methods are known for the production of ammonia and urea and among these, more particularly, is the one disclosed in the Italian Patent Specification No. 907 469, incorporated herein be reference.

Having reference to the latter patent, the integrated ammonia-urea method is carried out by utilizing the aqueous solution of ammonia, as obtained by absorbing with water the ammonia emerging from the reactor, to form ammonium carbamate with the carbon dioxide contained in the raw ammonia synthesis gases.

The thusly formed carbamate is subsequently fed to a reactor for the synthesis of urea, and therefrom an aqueous solution of carbamate and urea is discharged, the carbamate being then decomposed into its components in an ammonia stripper and the carbamate decomposition products together with the gaseous ammonia being recycled in the gaseous phase to the urea-synthesizing reactor.

The method as described previously, and in general all of the integrated methods, have the considerable defect that all the produced ammonia is used for the synthesis of urea.

Apparently, it is likely to occur that it is desired to produce more ammonia than that which is necessary for the urea, or that it is desired to produce less urea. The integrated methods used theretofore do not afford such a flexibility so that it is not possible in any way to vary at will the ammonia or the urea output.

An object of the present invention is a flexible integrated method for the production of urea and ammonia, by which it is possible to overcome the defects of the aforementioned conventional integrated methods, at least within a wide range.

The method which is the subject of the present invention consists in feeding part of a gaseous stream as obtained by hydrocarbon steam-reforming, which essentially consists of $CO_2$, $H_2$ and $N_2$, to a complementary decarbonating area wherein the $CO_2$ is partially removed, consistent with the quantity of urea one desires to produce, and then, after decarbonation, is sent together with the non-decarbonated portion directly to a $CO_2$-absorption vessel which is a part of an integrated urea-ammonia plant where the $CO_2$ is absorbed by an aqueous ammonia solution as obtained by absorption in water of the ammonia emerging from the synthesizing reactor.

In the $CO_2$-absorbing apparatus, ammonium carbamate is formed, which is fed to a urea-synthesizing reactor and from which a urea solution is discharged, which is treated in the conventional way.

The ammoniated solution, as obtained by absorption with water, which is in excess of that required for the absorption of $CO_2$ for the desired production of urea, is sent to a rectifying column, by the agency of which it is possible to obtain liquid ammonia.

When working according to the method of the present invention, it becomes thus possible to obtain liquid ammonia simultaneously with urea while varying the quantities of both ammonia and urea as produced over a wide range.

During the normal run of the installation as aforesaid, there will be simultaneous production of liquid ammonia and urea within the limits of the installation.

In this case, the complementary decarbonation installation will work under blander conditions than those usually provided for in the conventional ammonia production lines, in the sense that it will not be required to abate $CO_2$ down to a very low residual content and the heat waste will be reduced.

In the case of a stoppage of the urea section, the production of liquid ammonia can be maintained at the nominal value whereas the sections intended for the preparation of gas and ammonia synthesis will work under a reduced load. The complementary $CO_2$-absorption section and the section for the rectification of the ammoniated aqueous solution will operate, as it is obvious, under a full load; more particularly, all the converted gas will have to be decarbonated to about 1,000 parts of residual $CO_2$ per million.

If it is not required to produce liquid ammonia and it is desired to maintain the urea production rate at 100%, the complementary decarbonation and rectification sections will have to be put out of service whereas the urea section will function at full load. Obviously, the gas-preparation section and the ammonia synthesis section will operate under a reduced load.

An analysis of the operation of a synthesis compressor under the different run conditions has shown that no special problems exist as to regulation and that the machine can work under conditions of acceptable efficiency, even during the reduced-load runs.

It is apparent from the foregoing that the above described combined cycle affords a considerable degree of versatility.

The flexible integrated method of the present invention will now be illustrated in a nonlimiting manner by the diagram shown in the accompanying drawing.

BRIEF DESCRIPTION OF THE DRAWING

The drawing is a schematic representation of a system of apparatus through which my invention may be practiced.

Natural gas is fed through 1 to a sulfur-stripping section 2; after cooling through 3 the gas goes to a reforming stage 4 with steam 5, and, through 6, to a final reforming stage 8 with air fed in through 7.

The reformed gas emerging from 8, after cooling at 9, is forwarded to an apparatus 11 for the conversion of $CO_2$ into $CO_2$ through 10.

The gas emerging from the apparatus 11, composed essentially of $CO_2$, $N_2$ and $H_2$ is sent, after heating at 12 through the pipeline 13 to a $CO_2$-absorption system, the latter comprising an absorption apparatus 14 and a distillation apparatus 15 for recovering the solvent used for the absorption.

The gases which have been more or less deprived of $CO_2$ are sent through the duct 16 to become admixed with the gas of the duct 17 and then to the $CO_2$-absorbing section 18 through the duct 19 and the compressor 20.

In the $CO_2$-absorbing section 18 (carbamate reactor) carbon dioxide reacts in an almost complete way with the ammonia of the ammoniated solution as fed through 21, thus forming an ammonium carbamate solution which is discharged through the duct 22 and fed to the urea-synthesizing reactor 23.

The unreacted $CO_2$ fraction in the absorbing section 18 emerges from the top of this section together with the gas for the ammonia synthesis through the line 24 and is absorbed by a solution of ammonium carbonate rich with ammonia in the absorption section 25, forming a solution of ammonium carbamate which is discharged and introduced through 26 to the urea-synthesizing reactor 23.

The gases for the synthesis of ammonia, deprived of $CO_2$, which emerge from the apparatus 25 through the line 27 are fed to a methanation apparatus 28 where the $CO_2$ content is converted into methane.

The gases emerging from the methanation apparatus 28 are then admixed with the gases which had not been absorbed by the ammonia absorber 29 and which emerge through the line 30 and are essentially composed of $N_2$ and $H_2$ and then are fed through 31 to the dehydration installation wherefrom, upon compression, they are sent through 32 to the ammonia-synthesizing reactor, 33.

From the ammonia-absorbing section 29 a concentrated ammoniated solution is drawn which, partially through 21, is fed to the $CO_2$ absorption section, the remaining portion being sent to a rectification column 35 from which liquid ammonia is obtained.

In the urea-synthesizing reactor 23 the solution of ammonium carbamate is admixed with ammonia 34, coming from the urea purification section under a low pressure.

A portion of ammonia 36, coming from the low pressure purification stage of the urea solution is used for the dehydration of the ammonia synthesizing gas.

The urea solution is further treated in conventional fashion, being discharged through 37.

When working with the method of this invention, it is a surprising fact that the decrease of the partial pressure of $CO_2$ in the stream sent to the carbamate reactor as compared with the case where all the $CO_2$ is sent to said carbamate reactor, has no bearing on the conversion to carbamate, and this is contrary to the teachings of the present art according to which the $CO_2$ pressure is to be increased in order to increase the conversion rating.

An Example will now be given which aims at better illustrating the invention without limiting it in any way.

EXAMPLE

The starting data are:
Raw material: $CH_4$
Required outputs:
  Liquid $NH_3$: 400 metric tons a day
  Prilled urea: 1,000 metric tons a day
27,000 normal cubic meters an hour of natural gas, considered as 100% $CH_4$, are converted according to conventional techniques (primary reforming, secondary reforming, CO conversion at high and low temperature) into a mixture of converted gas having the following specification (on dry matter):
  Rate of flow: 146,500 norm. cubic meters an hour
  Pressure: 31.7 atmospheres
Composition:
  $H_2$: 61.30% by volume
  $N_2$: 20.00% by volume
  CO: 0.42% by volume
  $CO_2$: 17.35% by volume
  A: 0.24% by volume
  $CH_4$: 0.49% by volume From this latter gas, there are drawn from the main stream 74,500 normal cubic meters an hour, which are sent to the complementary decarbonation section 14, in the drawing, wherein 9,850 normal cubic meters of $CO_2$ are removed.

The following partially decarbonated gas is obtained, which is discharged through 16:
  Rate of flow: 64,600 norm. cu. meters
Composition:
  $H_2$: 70.65% by volume
  $N_2$: 23.00% by volume
  CO: 0.48% by volume
  A: 0.28% by volume
  $CH_4$: 0.56% by volume
  $CO_2$: 5.03% by volume This gas is subsequently combined with the main stream of the converted gas 17, and the result will be the following raw mixture of synthesis gas: Rate of flow: 136,650 normal cu. meters an hour
Composition:
  $H_2$: 65.86% by volume
  $N_2$: 21.40% by volume
  CO: 0.45% by volume
  A: 0.26% by volume
  $CH_4$: 0.53% by volume
  $CO_2$: 11.50% by volume This gas is compressed up to 200 kilograms per sq. centimeter and set first to the film absorbers for the absorption of CO in 18 and 25, and then to methanation in 28.

There are obtained 118,000 normal cubic meters an hour of methanized gas having the following composition (dry basis):
  $H_2$: 72.83% by volume
  $N_2$: 24.29% by volume
  A: 0.29% by volume
  $CH_4$: 1.09% by volume
  $NH_3$: 1.50% by volume This gas is combined with the recycled gas, 30, coming from the ammonia separation stage and the whole is dried by injection and washing with liquid $NH_3$, at 36.

More particularly, there are injected 7,750 kilograms an hour of liquid $NH_3$, the 93% of which is evaporated.

Lastly, a dry gas, 32, is obtained having the following specifications:
  Rate of flow: 584,000 norm. cu. meters an hour
Composition:
  $H_2$: 63.95% by volume
  $N_2$: 21.32% by volume
  A: 2.64% by volume
  $CH_4$: 9.46% by volume
  $NH_3$: 2.63% by volume This gas is fed to the $NH_3$ synthesis reactor 33.

The reacted gases, having the following specifications:
  Rate of flow: 530,000 norm. cu. meters an hour
Composition:
  $H_2$: 55.25% by volume
  $N_2$: 18.43% by volume
  A: 2.91% by volume
  $CH_4$: 10.41% by volume NH$_3$: 13.00% by volume are passed to the NH$_3$ film absorber wherein the NH$_3$ is separated until a residual content of 1% by volume is obtained.

There are produced 61,000 kilograms an hour of ammoniated solution having the following composition, on a weight basis:

NH$_3$: 80% by weight
H$_2$O: 20% by weight

Of this solution, 20,900 kilograms an hour are drawn and sent to the complementary rectification section, 35, where 16,700 kilograms an hour of liquid 91.9% NH$_3$, 38, which corresponds to 400 metric tons of NH$_3$ daily, are produced.

The remaining portion, 21, is sent to the CO$_2$ film absorber 18 already described, where 71,300 kilograms an hour are produced, of a carbamate solution having the following composition:

NH$_3$: 45.0% by weight
CO$_2$: 43.8% by weight
H$_2$O: 41.2% by weight

It should be noted that the NH$_3$ which is present is in excess by 32% relative to that bound to CO$_2$ in the form of carbamate and, on account of this excess, the vapour pressure of the carbamate is considerably diminished.

This solution is fed to the urea reactor which operates according to the integrated method as disclosed in the Italian Patent Specification No. 907 469, granted on the Feb. 15, 1972, incorporated herein by reference, and 41,670 kilograms an hour of urea are produced in such reactor, corresponding to 1,000 metric tons daily.

I claim:

1. In an integrated flexible method for the production of ammonia and urea comprising feeding a partially decarbonated gaseous stream consisting essentially of CO$_2$, N$_2$ and H$_2$ to an ammonium carbamate reactor to thereby form an ammonium carbamate solution, feeding said ammonium carbamate solution to a urea reactor, and recovering urea from said reactor, the improvement comprising:
    (a) reacting in a first reaction space of said ammonium carbamate reactor said partially decarbonated gaseous stream with a concentrated aqueous solution of ammonia to thereby form an ammonium carbamate solution;
    (b) feeding the unreacted partially decarbonated gaseous stream to a second reaction space of said ammonium carbamate reactor;
    (c) reacting said unreacted partially decarbonated gaseous stream with an ammonia rich ammonium carbonate solution to thereby form an ammonium carbamate solution;
    (d) feeding N$_2$ and H$_2$ obtained from said second reaction space to an ammonia systhesis reactor to thereby produce ammonia;
    (e) feeding said ammonia to an ammonia absorber to form a concentrated aqueous solution of ammonia; and
    (f) feeding a first portion of said concentrated aqueous solution of ammonia to said first reaction space of said ammonium carbamate reactor.
2. The method of claim 1 further comprising recovering liquid ammonia from a second portion of said concentrated aqueous solution of ammonia.

* * * * *